United States Patent [19]

Nieh

[11] Patent Number: 4,469,873
[45] Date of Patent: Sep. 4, 1984

[54] VINYL PYRIDINIUM MONOMERS

[75] Inventor: Edward C. Y. Nieh, Austin, Tex.

[73] Assignee: Texaco Inc., White Plains, N.Y.

[21] Appl. No.: 439,092

[22] Filed: Nov. 4, 1982

[51] Int. Cl.$^3$ .................................. C07D 213/02
[52] U.S. Cl. .................................. 546/344
[58] Field of Search .................................. 546/344

[56] References Cited

U.S. PATENT DOCUMENTS 4,212,820 7/1980 Hotchkiss et al. .................. 564/208

OTHER PUBLICATIONS

Functional Monomers (Marcel Dekker, Inc., New York, 1974) Yocum & Nyquist

Primary Examiner—Alan L. Rotman
Attorney, Agent, or Firm—Robert A. Kulason; Jack H. Park; Richard A. Morgan

[57] ABSTRACT

A new composition of matter is revealed, characterized by the general formula:

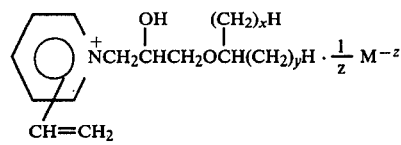

wherein x and y are integers of from 0 to 20 such that the sum of x plus y is an integer of from 8 to 20 and M is an anion of an organic or mineral acid having a valance of z.

This composition of matter is useful for the preparation of cationic polymeric surfactants, flocculants and coagulants.

5 Claims, No Drawings

VINYL PYRIDINIUM MONOMERS

BACKGROUND OF THE INVENTION

1. Field of the Invention

This invention relates to novel 3-(vinylpyridinium)-2-hydroxypropyl alkyl ether salts.

2. Description of the Prior Art

Quaternary ammonium monomers derived from acrylamide or methacrylamide are revealed in U.S. Pat. No. 4,212,820. The monomers, homopolymers, or interpolymers of these compounds may be used as additives in a number of processes or employed per se to produce a variety of manufactured articles.

The variety of monomers that can be produced is often limited by the competing uncontrollable polymerization reaction. In industrial practice it is typically necessary to produce a stable monomer which may later be subjected to a controlled polymerization process. Monomers which exist only fleetingly in an uncontrollable polymerization are of no use in a practical sense because they cannot be synthesized into useful products.

Converting vinyl pyridine monomers to their quaternary ammonium compounds is of considerable interest but heretofore has not been appreciably applied in the useful arts. The literature is replete with examples indicating spontaneous polymerization of vinyl pyridine occurring in polar solvent media under the influence of acid or alkylating reagents. Spontaneous, uncontrolled polymerization of vinyl pyridine monomers is mentioned in the following references:

1. V. A. Kabanov and V. A. Pelrovskaya Vysokomol. Soedin. BIO, 797(1968)
2. O. V. Kargina, M. V. Vlganovo, V. A. Kabanov and V. A. Kargin, Vyosokomol. Soedin., A9, 340(1967)
3. V. A. Kargin, V. A. Karbanov, K. F. Aliev and E. F. Rozvodovskii, Dokl. Akad. Nauk SSSR, 160, 604(1965)
4. I. Iwatsu, T. Kobubee, K. Motomatsu, M. Tsugi and Y. Yamashita, Makromol. Chem., 120, 154(1968)
5. I. Miehke and H. Ringsorf, J. Polymer Sci., Pt., C, 31,107 (1970); Polymer Letters 9, 1 (1971); Makromol. Chem., 142, 319 (1971)
6. J. L. Salamone, B. Snider, and W. L. Fitch, Polymer Letters 9, 13 (1971); J. Polymer Sci., P A1, 9 1493 (1971)

The reference *Functional Monomers*, Volume 2, by R. H. Nocum & E. B. Nyquist, Marcel Dekker Inc., N.Y. (1974) establishes that (1) successful alkylation of vinyl pyridine to a quaternary ammonium monomer is unexpected (p. 632); (2) polymers containing the pyridinium moiety were made by alkylation of polymer containing pyridine (p. 629), and (3) polymers containing the pyridinium quaternary ammonium group are useful (p. 648).

It is the object of the present invention to prepare a new class of stable surface active quaternary pyridinium monomer which can be later controllably polymerized into a variety of useful products such as surfactants, flocculants and coagulants.

SUMMARY OF THE INVENTION

The invention is a series of vinyl pyridine monomers of the general formula:

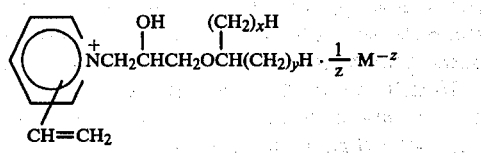

wherein x and y are each integers of from 0 to 20 such that the sum of x plus y is an integer of from 8 to 20 and M is an anion of an organic or mineral acid having a valence of z.

DESCRIPTION OF THE PREFERRED EMBODIMENTS

The compounds of the present invention may be prepared utilizing a number of known synthetic techniques. One preferred mode of preparation involves reacting the appropriate glycidyl alkyl ether with the corresponding vinyl pyridinium salts and an organic or mineral acid in an alcoholic medium.

The reaction may be depicted as follows where x, y, z and M are defined above. The reaction is carried out in polar solvent and it has been found that an excess of acid is helpful in stabilizing the product in alcoholic solvents. Typically, convenient solvents found to be of use in synthesizing monomers of the present invention are formic acid, acetic acid and propionic acid and mixtures thereof or mixtures of one of those acids and a lower alcohol such as methanol, ethanol or isopropyl alcohol and mixtures thereof.

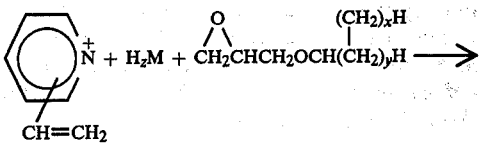

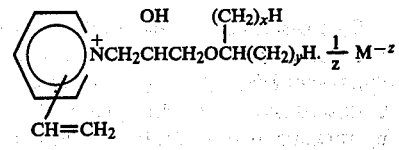

The vinyl pyridinium salt and glycidyl alkyl ether are well known in the art. The glycidyl alkyl ethers of the present invention are commercially available, and in the examples is shown the use of the glycidyl lauryl ether, and a commercially available mixture of glycidyl dodecyl ether and glycidyl tetradecyl ether.

The reaction of an oxide with a basic nitrogen atom such as a tertiary amine to form a quaternary moiety is well known to those skilled in the art, and needs little explanation. This reaction may be carried out over a wide temperature range, typically 30° C. to 80° C. The reaction is preferably conducted in closed vessel under inert atmosphere. Usually the acid is first added to the vinyl pyridine followed by addition of glycidyl alkyl ether. However, acid, vinyl pyridine and glycidyl alkyl ether may be reacted by simultaneous addition to one another.

A wide variety of organic or inorganic acids may be employed, and thus M in the above formula defining the final products may represent anionic radicals such as halo (including chloride, bromide, or iodide) acetate, lactate, gluconate, sulfate, nitrate, alkylsulfate, alkyl and arylsulfonates (e.g., methyl-, ethyl-, propyl-, butyl-benzenesulfonate), formate, propionate, oxalate, phenylsulfonate, benzoate, borate, etc. Preferred acids include acetic acid, hydrochloric acid, and sulfuric acid.

Usually the reaction between the vinyl pyridine acid and glycidyl alkyl ether is conducted in polar solvent such as methanol, ethanol, isopropanol, and the like being preferred.

The following Examples illustrate preparation of typical compounds falling within the scope of the invention. It is understood that these Examples are merely illustrative and that the invention is not to be limited thereto.

EXAMPLE 1

In a 500 ml three-neck flask equipped with stirrer, thermometer and addition funnel, acetic acid (24 g) 4-vinyl pyridine (42 g), glycidyl lauryl ether (96.8 g) and methanol (162 g) were admixed while the pot temperature was kept below 20° C. with external cooling. The reaction mixture was heated to 50° C. and digested at 50° C. for a period of five hours. Nuclear magnetic resonance spectra (nmr) taken immediately after the reaction were consistent with those expected from the desired 3-(4-vinyl pyridinium)-2-hydroxypropyl lauryl ether acetate. The conversion of the vinyl pyridine was essentially completed as shown by only one set of aromatic proton signals at delta 57.7 and delta 8.55 corresponding to the para substituted alkylated pyridinium moiety. However, after standing at ambient temperature for several days the nmr spectra showed two sets of aromatic proton signals. One set corresponds to the N-alkylated pyridinium ion described above and the other set at delta 8.0 and delta 8.68 corresponds to the unreacted 4-vinyl pyridine. The relative area of these two sets of signals indicated that a 25% reversal to the starting 4-vinyl pyridine had occurred.

EXAMPLE 2

By a procedure similar to that described in Example 1, acetic acid (186 g), 4-vinyl pyridine (42 g) and glycidyl lauryl ether (96.8 g) were reacted at 50° C. for a period of five hours. Analysis of the resulting solutions by titration with hydrobromic acid in acetic acid indicated that 98.7% conversion* to the desired 3-(4-vinyl pyridinium)-2-hydroxypropyl lauryl ether acetate had occurred. The product remains stable in the presence of excess acetic acid. The surface tension and the interfacial tension (water/light mineral oil) of clear aqueous solutions containing 1%, 0.1% and 0.01% of the surface active monomer were measured and results are summarized below:

| Concentration of monomer % | Surface Tension dyne/cm | Interfacial Tension dyne/cm |
|---|---|---|
| 1 | 30.6 | 7.1 |
| 0.1 | 30.1 | 20.0 |
| 0.01 | 33.4 | 29.5 |

*The expected alkylation reaction would convert two equivalents of hydrobromic acid titratable bases (i.e., pyridine and glycidyl alkyl ether) to one equivalent of hydrobromic acid titratable base (i.e., acetate anion). Accordingly, % conversion for reaction with equal molar quantities of vinyl pyridine and glycidyl alkyl ether is calculated according to an equation below:

$$\% \text{ conversion} = \left(1 - \frac{B_1 - B_o}{B_o}\right) \times 100\%$$

where $B_1$ is meq/g of hydrobromic aid titratable bases at the end of the reaction.

$B_o$ is meq/g of acetate anion for 100% conversion.

EXAMPLE 3

By a procedure similar to that described in Example 1, acetic acid (159 g), 2-vinyl pyridine (42 g), and glycidyl alkyl ether (117.2 g) equivalent weight 293, Proctor and Gamble, Epoxide No. 8, a mixture of glycidyl tetradecyl ether and glycidyl dodecyl ether) were reacted at 50° C. for a period of five hours. Analysis of the resulting solution by titration with hydrobromic acid in acetic acid indicated that 92.0% conversion to the desired 3-(2-vinyl pyridinium)-2-hydroxypropyl alkyl ether acetate had occurred. The product remained stable in excess acetic acid. The surface tension and interfacial tension (water/light mineral oil) of the surface active monomers were measured. Results are summarized below.

| Concentration of monomer % | Surface Tension dyne/cm | Interfacial Tension dyne/cm |
|---|---|---|
| 1 | 32.3 | 6.4 |
| 0.1 | 32.6 | 11.2 |
| 0.01 | 31.8 | 20.0 |

EXAMPLE 4

By a procedure similar to that described in Example 1, acetic acid (186 g), 4-vinyl pyridine (42 g) and glycidyl alkyl ether (117.2 g equivalent weight 293, Proctor and Gamble, Epoxide No. 8) were reacted at 50° C. for a period of five hours. Analysis of the resulting solution by titration with hydrobromic acid in acetic acid indicated 96.5% conversion to the desired N-alkylated pyridinium acetate had occurred. The product remained stable in the presence of excess acetic acid. The surface tension and the interfacial tension of clear aqueous solutions containing 1%, 0.1% and 0.01% of the surface active monomer were measured at ambient temperature. Results are summarized below:

| Concentration of monomer % | Surface Tension dyne/cm | Interfacial Tension dyne/cm |
|---|---|---|
| 1 | 31.5 | 6.9 |
| 0.1 | 31.6 | 14.8 |
| 0.01 | 32.8 | 25.2 |

EXAMPLE 5

A homopolymer of molecular weight ranging from 1000 to 5000 is synthesized from products of Example 2. The aqueous solution of the cationic surface active polymer is useful as a flocculant for anionic surfactants. 250 g of several 0.1% aqueous solutions of anionic surfactants, namely, sodium lauryl sulfate, NEODOL ® 25-5 ether sulfate (NEODOL ® 25-5 is a 5 mole ethoxylate of a $C_{12}$–$C_{15}$ primary alcohol), and Conoco C-550 (linear alkylbenzene sulfonate with an average carbon chain length of 11.4 and molecular weight of 340) are treated with 1 ml of 1% aqueous solution of the above mentioned cationic surface active polymer. In each case, flocculation occurs instantaneously. After removing the precipitation by filtration, the anion surfactant in the filtrate is found to be substantially reduced.

EXAMPLE 6

In a field in which the primary production has already been exhausted, an injection well is completed in the hydrocarbon-bearing formation and perforations are formed between the interval of 6890–6910 feet. A production well is drilled approximately 415 feet distance from the injection well, and perforations are similarly made in the same hydrocarbon-bearing formation at 6895–6915 feet.

The hydrocarbon-bearing formation in both the injection well and the production well is hydraulically fractured using conventional techniques, and a gravel-sand mixture is injected into the fracture to hold it open and prevent healing of the fracture.

In the next step, oil field water at a temperature of 75° F. containing dissolved therein 1% by weight of a copolymer of molecular weight ranging from 10.000 to 80.000 synthesized from the product of Example 2 (5%) and acrylamide (95%) is injected via the injection well into the formation at a pressure of about 1300 psig and at the rate of 1.05 barrels per minute. Injection of the driving fluid continues at the rate of 1.05 barrels per minute and at the end of 67 days, a substantial production of petroleum is achieved.

The principle of the invention and the best mode contemplated for applying that principle have been described. It is to be understood that the foregoing is illustrative only and that other means and techniques can be employed without parting from the true scope of the following claims.

What is claimed is:

1. A composition of matter of the general formula:

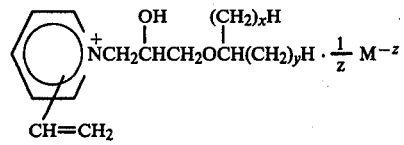

wherein x and y are each integers of from 0 to 20 such that the sum of x plus y is an integer of from 8 to 20 and M is an anion of an organic or mineral acid having a valence of z wherein M is selected from the group consisting of chloride, bromide, iodide, lactate, gluconate, sulfate, nitrate, alkylsulfate, alkylsulfonate, arylsulfonate, formate, propionate, oxalate, phenylsulfonate, benzoate, borate and acetate.

2. The composition of matter of claim 1 wherein M is acetate.

3. The composition of matter of claim 1 wherein x plus y is an integer of from 11 to 16.

4. The composition of matter of claim 1 wherein x plus y is 11.

5. The composition of matter of claim 1 wherein M is selected from the group consisting of acetate, chloride and sulfate.

* * * * *